(12) United States Patent
Mitchell

(10) Patent No.: US 6,966,929 B2
(45) Date of Patent: Nov. 22, 2005

(54) ARTIFICIAL VERTEBRAL DISK REPLACEMENT IMPLANT WITH A SPACER

(75) Inventor: Steve Mitchell, Pleasant Hill, CA (US)

(73) Assignee: St. Francis Medical Technologies, Inc., Alameda, CA (US)

( * ) Notice: Subject to any disclaimer, the term of this patent is extended or adjusted under 35 U.S.C. 154(b) by 0 days.

(21) Appl. No.: 10/685,011

(22) Filed: Oct. 14, 2003

(65) Prior Publication Data

US 2004/0138750 A1 Jul. 15, 2004

Related U.S. Application Data

(60) Provisional application No. 60/422,022, filed on Oct. 29, 2002.

(51) Int. Cl.$^7$ ................................................ A61B 17/58
(52) U.S. Cl. ...................................................... 623/17.11
(58) Field of Search ........................... 623/17.13, 17.14, 623/17.15, 17.16

(56) References Cited

U.S. PATENT DOCUMENTS 2,456,806 A    12/1948   Wolffe (Continued)

FOREIGN PATENT DOCUMENTS

| CA | 2015507 | 1/1991 |
|---|---|---|
| DE | 3113142 | 1/1982 |
| DE | 4012622 | 7/1991 |
| EP | 0307241 B1 | 3/1989 |
| EP | 0322334 | 6/1989 |
| FR | 2722980 | 7/1994 |
| FR | 2705227 | 11/1994 |
| FR | 2707864 | 1/1995 |
| FR | 2717066 | 1/1995 |
| FR | 2717068 | 9/1995 |
| FR | 2722088 | 1/1996 |
| FR | 2724554 | 3/1996 |
| FR | 2722088 | 1/1996 |
| FR | 2724554 | 3/1996 |
| FR | 2730156 A1 | 8/1996 |
| FR | 2780269 A1 | 12/1999 |
| FR | 2806614 A1 | 9/2001 |
| GB | 780652 | 8/1957 |
| WO | WO 90/00037 | 1/1990 |
| WO | WO 95/31158 A | 11/1995 |
| WO | WO 99/26562 | 6/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | 01/01893 A1 | 1/2001 |

OTHER PUBLICATIONS

*Ceramic Interspinous Block (CISB) Assisted Anterior Interbody Fusion*, Haruo Tsuji, Norikazu Hirano, Hiroshi Ohsima, Hirokazu Ishihara, Hisao Matsui,and Yohihiko Hayashi, Journal of Spinal Disorders vol. 3, No. 1, pp 77–86, c1990 Raven Press, Ltd., New York.

*Instrumentation and Implan for Spinal Surgery*,J. Dabb, Diary of the XVIIIth Scientific Meeting of the PTO Tr/Pamietnik XVIII Zjardu Naukowego PTO Tr/PZ,WL, Warszawa, Link America Inc., 1971, 665.

*Spinal Stenosis and Neurogenic Claudication*, Richard W. Porter, MD, FRCS,FRCSE, SPINE vol. 21, No. 17, pp 2046–2052, c1996, Lippincott–Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K. Walsh, FRCS, SPINE vol. 22, No. 16, pp 1819–1827, c1997, Lippincott Raven, Publishers.

Primary Examiner—Eduardo C. Robert
Assistant Examiner—Annette Reimers
(74) Attorney, Agent, or Firm—Fliesler Meyer LLP

(57) ABSTRACT

The present invention is directed to a device that can be placed between two vertebrae. The implant is characterized by having a first plate and a second plate with a spacer therebetween. The spacer fits within cavities on each of the first and second plate.

89 Claims, 10 Drawing Sheets

U.S. PATENT DOCUMENTS

| | | |
|---|---|---|
| 2,677,369 A | 5/1954 | Knowles |
| 3,648,691 A | 3/1972 | Lumb |
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,636,217 A | 1/1987 | Ogilvie |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buttner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Fuhrmann et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,352,225 A | 10/1994 | Yuan et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A | 3/1995 | Kozak et al. |
| 5,401,269 A * | 3/1995 | Buttner-Janz et al. ... 623/17.15 |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A * | 9/1996 | Buttner-Janz ............ 623/17.15 |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,609,634 A | 3/1997 | Voydeville |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |

| Patent No. | Date | Inventor(s) |
|---|---|---|
| 5,645,598 A | 7/1997 | Brosnahan, III |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A | 12/1997 | Margulies |
| 5,702,449 A | 12/1997 | McKay |
| 5,702,450 A | 12/1997 | Bisserie |
| 5,702,454 A | 12/1997 | Baumgartner |
| 5,702,455 A | 12/1997 | Saggar |
| 5,716,415 A | 2/1998 | Steffee |
| 5,716,416 A | 2/1998 | Lin |
| 5,741,253 A | 4/1998 | Michelson |
| 5,755,732 A | 5/1998 | Green et al. |
| 5,755,796 A | 5/1998 | Ibo et al. |
| 5,755,798 A | 5/1998 | Papavero et al. |
| 5,766,252 A | 6/1998 | Henry et al. |
| 5,772,661 A | 6/1998 | Michelson |
| 5,776,196 A | 7/1998 | Matsuzaki et al. |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,797,909 A | 8/1998 | Michelson |
| 5,800,438 A | 9/1998 | Tuke et al. |
| 5,800,550 A | 9/1998 | Sertich |
| 5,824,093 A | 10/1998 | Ray et al. |
| 5,824,094 A | 10/1998 | Serhan et al. |
| 5,827,328 A | 10/1998 | Buttermann |
| 5,836,948 A | 11/1998 | Zucherman et al. |
| 5,860,973 A | 1/1999 | Michelson |
| 5,860,977 A | 1/1999 | Zucherman et al. |
| 5,865,845 A | 2/1999 | Thalgott |
| 5,865,846 A | 2/1999 | Bryan et al. |
| 5,876,404 A | 3/1999 | Zucherman et al. |
| 5,885,292 A | 3/1999 | Moskovitz et al. |
| 5,885,299 A | 3/1999 | Winslow et al. |
| 5,888,222 A | 3/1999 | Coates et al. |
| 5,888,224 A | 3/1999 | Beckers et al. |
| 5,888,226 A | 3/1999 | Rogozinski |
| 5,891,147 A | 4/1999 | Moskovitz et al. |
| 5,893,889 A | 4/1999 | Harrington |
| 5,893,890 A | 4/1999 | Pisharodi |
| 5,895,426 A | 4/1999 | Scarborough et al. |
| 5,895,427 A | 4/1999 | Kuslich et al. |
| 5,895,428 A | 4/1999 | Berry |
| 5,899,941 A | 5/1999 | Nishijima et al. |
| 5,906,616 A | 5/1999 | Pavlov et al. |
| 5,919,235 A | 7/1999 | Husson et al. |
| 5,928,284 A | 7/1999 | Mehdizadeh |
| 5,944,754 A | 8/1999 | Vacanti |
| 5,945,115 A | 8/1999 | Dunn et al. |
| 5,961,554 A | 10/1999 | Jamson et al. |
| 5,964,807 A | 10/1999 | Gan et al. |
| 5,976,186 A | 11/1999 | Bao et al. |
| 5,980,572 A | 11/1999 | Kim et al. |
| 5,984,967 A | 11/1999 | Zdeblick et al. |
| 5,989,291 A | 11/1999 | Ralph et al. |
| 6,001,130 A | 12/1999 | Bryan et al. |
| 6,004,573 A | 12/1999 | Rathi et al. |
| 6,005,162 A | 12/1999 | Constantz |
| 6,019,792 A | 2/2000 | Cauthen |
| 6,019,793 A | 2/2000 | Perren et al. |
| 6,022,376 A | 2/2000 | Assell et al. |
| 6,039,761 A | 3/2000 | Li et al. |
| 6,039,763 A | 3/2000 | Shelokov |
| 6,042,582 A | 3/2000 | Ray |
| 6,045,579 A | 4/2000 | Hochshuler et al. |
| 6,045,580 A | 4/2000 | Scarborough et al. |
| 6,048,342 A | 4/2000 | Zucherman et al. |
| 6,051,648 A | 4/2000 | Rhee et al. |
| 6,068,630 A | 5/2000 | Zucherman et al. |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochshuler et al. |
| 6,086,613 A | 7/2000 | Camino et al. |
| 6,090,112 A | 7/2000 | Zucherman et al. |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,110,210 A | 8/2000 | Norton et al. |
| 6,111,164 A | 8/2000 | Rainey et al. |
| 6,113,637 A | 9/2000 | Gill et al. |
| 6,113,638 A | 9/2000 | Williams et al. |
| 6,113,639 A | 9/2000 | Ray et al. |
| 6,120,502 A | 9/2000 | Michelson |
| 6,120,503 A | 9/2000 | Michelson |
| 6,123,705 A | 9/2000 | Michelson |
| 6,126,689 A | 10/2000 | Brett |
| 6,127,597 A | 10/2000 | Beyar et al. |
| 6,129,763 A | 10/2000 | Chauvin et al. |
| 6,132,430 A | 10/2000 | Wagner |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,149,650 A | 11/2000 | Michelson |
| 6,149,652 A | 11/2000 | Zucherman et al. |
| 6,149,686 A | 11/2000 | Kuslich et al. |
| 6,152,926 A | 11/2000 | Zucherman et al. |
| 6,156,038 A | 12/2000 | Zucherman et al. |
| 6,156,067 A | 12/2000 | Bryan et al. |
| 6,159,215 A | 12/2000 | Urbahns et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,206,922 B1 | 3/2001 | Zdeblick et al. |
| 6,210,412 B1 | 4/2001 | Michelson |
| 6,224,595 B1 | 5/2001 | Michelson |
| 6,224,631 B1 | 5/2001 | Kohrs |
| 6,228,118 B1 | 5/2001 | Gordon |
| 6,231,609 B1 | 5/2001 | Mehdizadeh |
| 6,234,705 B1 | 5/2001 | Troxell |
| 6,235,030 B1 | 5/2001 | Zucherman et al. |
| 6,238,397 B1 | 5/2001 | Zucherman et al. |
| 6,241,769 B1 | 6/2001 | Nicholson et al. |
| 6,241,770 B1 | 6/2001 | Michelson |
| 6,241,771 B1 | 6/2001 | Gresser et al. |
| 6,245,072 B1 | 6/2001 | Zdeblick et al. |

| Patent No. | Date | Inventor |
|---|---|---|
| 6,245,108 B1 | 6/2001 | Biscup |
| 6,261,296 B1 | 7/2001 | Aebi et al. |
| 6,264,655 B1 | 7/2001 | Pisharodi |
| 6,264,656 B1 | 7/2001 | Michelson |
| 6,264,695 B1 | 7/2001 | Stoy |
| 6,270,498 B1 | 8/2001 | Michelson |
| 6,277,149 B1 | 8/2001 | Boyle et al. |
| 6,280,444 B1 | 8/2001 | Zucherman et al. |
| 6,280,475 B1 | 8/2001 | Bao et al. |
| 6,287,343 B1 | 9/2001 | Kuslich et al. |
| 6,296,664 B1 | 10/2001 | Middleton |
| 6,296,665 B1 | 10/2001 | Strnad et al. |
| 6,302,914 B1 | 10/2001 | Michelson |
| 6,309,421 B1 | 10/2001 | Pisharodi |
| 6,311,562 B1 | 11/2001 | Hanada |
| 6,315,795 B1 | 11/2001 | Scarborough et al. |
| 6,315,797 B1 | 11/2001 | Middleton |
| 6,325,827 B1 | 12/2001 | Lin |
| 6,332,882 B1 | 12/2001 | Zucherman et al. |
| 6,332,883 B1 | 12/2001 | Zucherman et al. |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zucherman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoech et al. |
| 6,425,920 B1 | 7/2002 | Hamada |
| 6,432,106 B1 | 8/2002 | Fraser |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zucherman et al. |
| 6,451,020 B1 | 9/2002 | Zucherman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,475,219 B1 | 11/2002 | Shelokov |
| 6,478,796 B2 | 11/2002 | Zucherman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B2 | 12/2002 | Besselink |
| 6,500,178 B2 | 12/2002 | Zucherman et al. |
| 6,500,205 B1 | 12/2002 | Michelson |
| 6,503,279 B1 | 1/2003 | Webb et al. |
| 6,514,256 B2 | 2/2003 | Zucherman et al. |
| 6,517,580 B1 | 2/2003 | Ramadan et al. |
| 6,520,993 B2 | 2/2003 | James et al. |
| 6,520,996 B1 | 2/2003 | Manasas et al. |
| 6,524,312 B2 | 2/2003 | Landry et al. |
| 6,527,773 B1 | 3/2003 | Lin et al. |
| 6,527,804 B1 | 3/2003 | Gauchet et al. |
| 6,527,806 B2 | 3/2003 | Ralph et al. |
| 6,530,933 B1 | 3/2003 | Yeung et al. |
| 6,530,955 B2 | 3/2003 | Boyle et al. |
| 6,540,785 B1 | 4/2003 | Gill et al. |
| 6,547,823 B2 | 4/2003 | Scarborough et al. |
| 6,548,002 B2 | 4/2003 | Gresser et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,569,201 B2 | 5/2003 | Moumene et al. |
| 6,572,653 B1 | 6/2003 | Simonson |
| 6,572,654 B1 | 6/2003 | Santilli |
| 6,575,982 B1 | 6/2003 | Bonutti |
| 6,576,016 B1 | 6/2003 | Hochshuler et al. |
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,682,562 B2 | 1/2004 | Viart et al. |
| 6,706,070 B1 | 3/2004 | Wagner et al. |
| 6,740,118 B2 | 5/2004 | Eisermann et al. |
| 6,755,841 B2 | 6/2004 | Fraser et al. |
| 6,770,095 B2 | 8/2004 | Grinberg et al. |
| 2001/0012938 A1 | 8/2001 | Zucherman et al. |
| 2002/0128715 A1 * | 9/2002 | Bryan et al. ............. 623/17.15 |
| 2003/0208273 A1 * | 11/2003 | Eisermann et al. ...... 623/17.14 |
| 2004/0073313 A1 * | 4/2004 | Link et al. ............... 623/17.15 |
| 2004/0106998 A1 | 6/2004 | Ferree |
| 2004/0117022 A1 * | 6/2004 | Marnay et al. .......... 623/17.16 |
| 2004/0138750 A1 | 7/2004 | Mitchell |
| 2004/0143332 A1 | 7/2004 | Krueger et al. |

* cited by examiner

US 6,966,929 B2

ARTIFICIAL VERTEBRAL DISK REPLACEMENT IMPLANT WITH A SPACER

CLAIM OF PRIORITY

This application claims priority to U.S. Provisional Application No. 60/422,022, which was filed Oct. 29, 2002, entitled "ARTIFICIAL VERTEBRAL DISK REPLACEMENT IMPLANT WITH A SPACER AND METHOD," which is incorporated herein by reference.

CROSS-REFERENCE TO RELATED APPLICATIONS

This application is related to U.S. Provisional Application No. 60/422,039, filed Oct. 29, 2002, entitled "ARTIFICIAL VERTEBRAL DISK REPLACEMENT IMPLANT WITH TRANSLATING PIVOT POINT AND METHOD", U.S. patent application Ser. No. 10/684,669, filed Oct. 14, 2003, entitled "ARTIFICIAL VERTEBRAL DISK REPLACEMENT IMPLANT WITH TRANSLATING PIVOT POINT AND METHOD", U.S. Provisional Application No. 60/422,021, filed Oct. 29, 2002, entitled "ARTIFICIAL VERTEBRAL DISK REPLACEMENT IMPLANT WITH CROSSBAR SPACER AND METHOD", U.S. patent application Ser. No. 10/684,668, filed Oct. 14, 2003, entitled "ARTIFICIAL VERTEBRAL DISK REPLACEMENT IMPLANT WITH CROSSBAR SPACER AND METHOD", U.S. Provisional Application No. 60/422,011, filed Oct. 29, 2002, entitled "TOOLS FOR IMPLANTING AN ARTIFICIAL VERTEBRAL DISK AND METHOD", and U.S. patent application Ser. No. 10/685,134, filed Oct. 14, 2003, entitled "TOOLS FOR IMPLANTING AN ARTIFICIAL VERTEBRAL DISK AND METHOD", which are all incorporated hereby by this reference.

FIELD OF THE INVENTION

This invention relates to an artificial vertebral disk replacement and method.

BACKGROUND OF THE INVENTION

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of older people. Pain associated with such conditions can be relieved by medication and/or surgery. Of course, it is desirable to eliminate the need for major surgery for all individuals, and, in particular, for the elderly.

More particularly, over the years, a variety of intervertebral implants have been developed in an effort to relieve the pain associated with degenerative and dysfunctional disk conditions. For example, U.S. Pat. No. 4,349,921 to Kuntz discloses an intervertebral disk prosthesis.

U.S. Pat. No. 4,714,469 to Kenna discloses a spinal implant that fuses vertebrae to the implant. The implant has a rigid body that fits between the vertebra with a protuberance extending from a vertebral contacting surface and extends into the vertebral body.

U.S. Pat. No. 5,258,031 to Salib et al. discloses another prosthetic disk with a ball that fits into a socket.

U.S. Pat. Nos. 5,425,773 and 5,562,738 are related patents to Boyd et al. that disclose a disk arthroplasty device for replacement of the spinal disk. A ball-and-socket are provided to enable rotation.

U.S. Pat. No. 5,534,029 to Shima discloses an articulated vertebral body spacer with a pair of upper and lower joint pieces inserted between the vertebra. An intermediate layer is provided to allow for movement between the upper joint piece and the lower joint piece.

U.S. Pat. No. 5,782,832 to Larsen et al. discloses a two-piece ball-and-socket spinal implant with upper and lower plates for insertion within the intervertebral space.

U.S. Pat. No. 6,156,067 to Bryan et al. discloses a prosthesis having two plates with a nucleus there between.

None of these solutions provide an implant that restores a wide range of natural movement.

Accordingly, there needs to be developed implants for alleviating such conditions, and for restoring natural movement.

SUMMARY OF THE INVENTION

An embodiment of the present invention is directed to providing an implant for alleviating discomfort associated with the spinal column. The implant is characterized by having a first plate and a second plate with a spacer therebetween. The spacer fits within cavities on each of the first and second plate.

Other aspects, objects, features and elements of embodiments of the invention are described or are evident from the accompanying specification, claims and figures.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims.

Figure 1A:
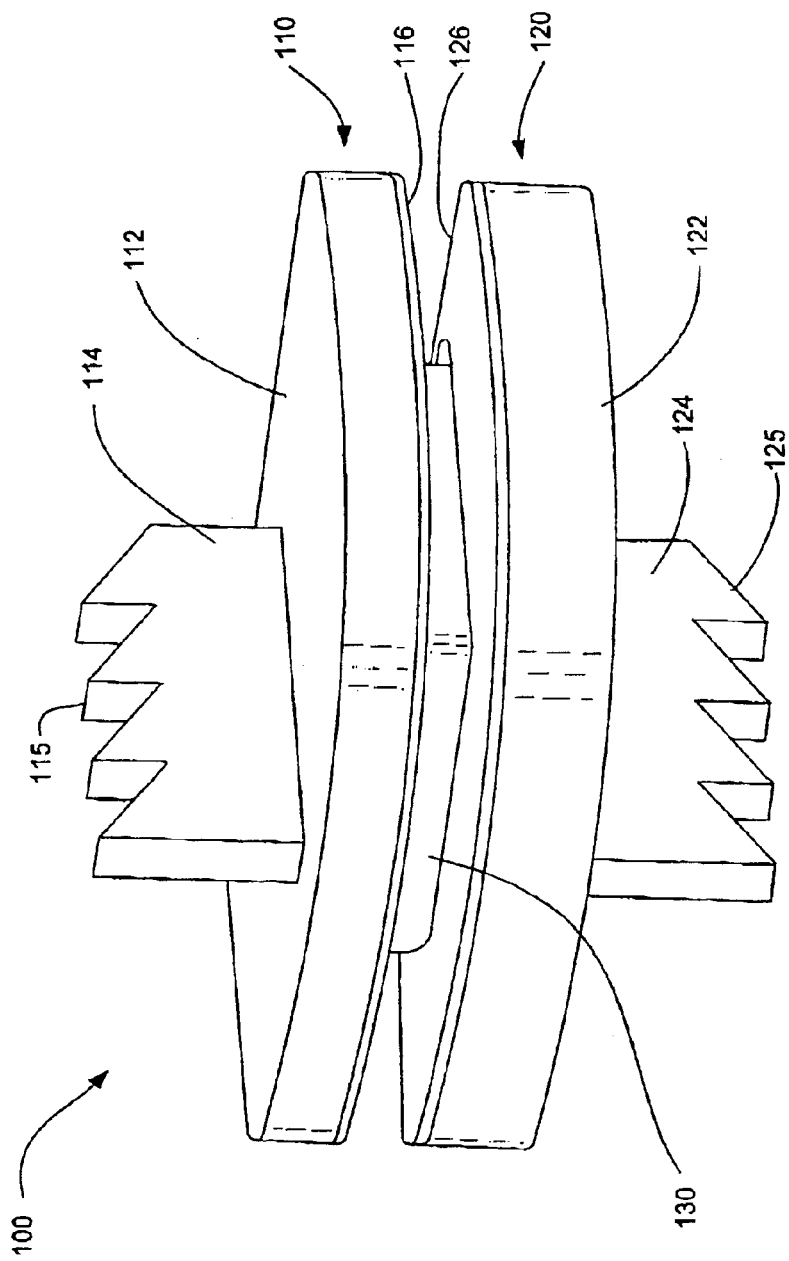
FIG. 1A is a side perspective view of an embodiment of the assembled implant of the invention.

Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference FIG. 1A shows an embodiment of the implant 100 of the invention. The implant 100 has a first part 110 that is configured to mate with a first vertebra and a second part 120 that is configured to mate with a second vertebra. The first part 110 is a first or upper plate and the second part 120 is a second or lower plate. A third part 130 sits between the first part 110 and the second part 120. The third part 130 acts as a spacer between the first part 110 and the second part 120 and facilitates pivotal movement of the first plate 110 and second plate 120, relative to each other.

The upper plate 110 has a first surface 112 from which a keel 114 extends. The first surface 112, or upper surface, abuts the vertebral body when the implant 100 is implanted. The first keel 114 extends into the vertebral body to anchor the implant into position. The keel 114 includes teeth 115 that assist in keeping the keel in position once the implant 100 is positioned between vertebral bodies. Generally, in a preferred embodiment that is to be implanted by an anterior approach, the teeth 115 point anteriorly in order to prevent the implant 100 from moving in an anterior direction. The second surface 116, or lower surface, engages the third part 130 of the implant and faces the second plate 120. The second surface 116 can form a planar surface that is parallel to the first surface 112, or can form a planar surface that is unparallel to the first surface 112 in order, in one embodiment, to allow the first plate 110 and the second plate 120 to be able to pivot to a greater degree with respect to each other. It is to be understood that other factors such as the height of the spacer 130 can also be adjusted in order to increase the degree that the first plate 110 and the second plate 120 can pivot relative to each other.

When the implant is implanted between vertebral bodies the planar surfaces corresponding to the first surface 112 and the second surface 116 of the first plate 110 lie within, or substantially within, the axial plane of the body while the first keel 114 (which is at or near a 90° angle from the surfaces 112, 116) is aligned within the sagittal plane of the body.

The lower plate 120 has a first surface 122 from which a keel 124 extends. The first surface 122, or lower surface, abuts the vertebral body when the implant 100 is implanted. The second keel 124 extends into the vertebral body to anchor the implant into position. The keel 124 includes teeth 125 that assist in keeping the keel in position once the implant 100 is positioned between vertebral bodies. Generally, in a preferred embodiment that is to be implanted by an anterior approach, the teeth 125 point anteriorly in order to prevent the implant 100 from moving in an anterior direction. The second surface 126, or upper surface, engages the third part 130 of the implant and faces the first plate 110. The second surface 126 can form a planar surface that is parallel to the first surface 122, or can form a planar surface that is not parallel to the first surface in order, in one embodiment, to allow the first plate 110 and the second plate 120 to be able to pivot or rotate to a greater degree with respect to each other. The first surface 112 of the first plate 110 can form a planar surface that is parallel to a planar surface formed by the first surface 122 of the second plate 120 when the implant 100 is assembled and is in a neutral position (i.e., the position where the first plate 110 has not rotated relative to the second plate 120). Alternatively, the first surface 112 of the first plate 110 can form a planar surface that is not parallel to the planar surface of the first surface 122 of the second plate 120 when the implant 100 is assembled and in a neutral position in order to accommodate the geometry of adjacent end plates of adjacent vertebral bodies. Such non-parallel surface in certain situations could eliminate a need to modify the surface of the end plates in order to accommodate the implant 100.

As with the first plate, when the implant is implanted between vertebral bodies the planar surfaces corresponding to the first surface 122 and the second surface 126 of the second plate 120 lie within, or substantially within, the axial plane of the body while the second keel 124 (which is at or near a 90° angle from the surfaces 122, 126) is aligned within the sagittal plane of the body.

Figure 1B:
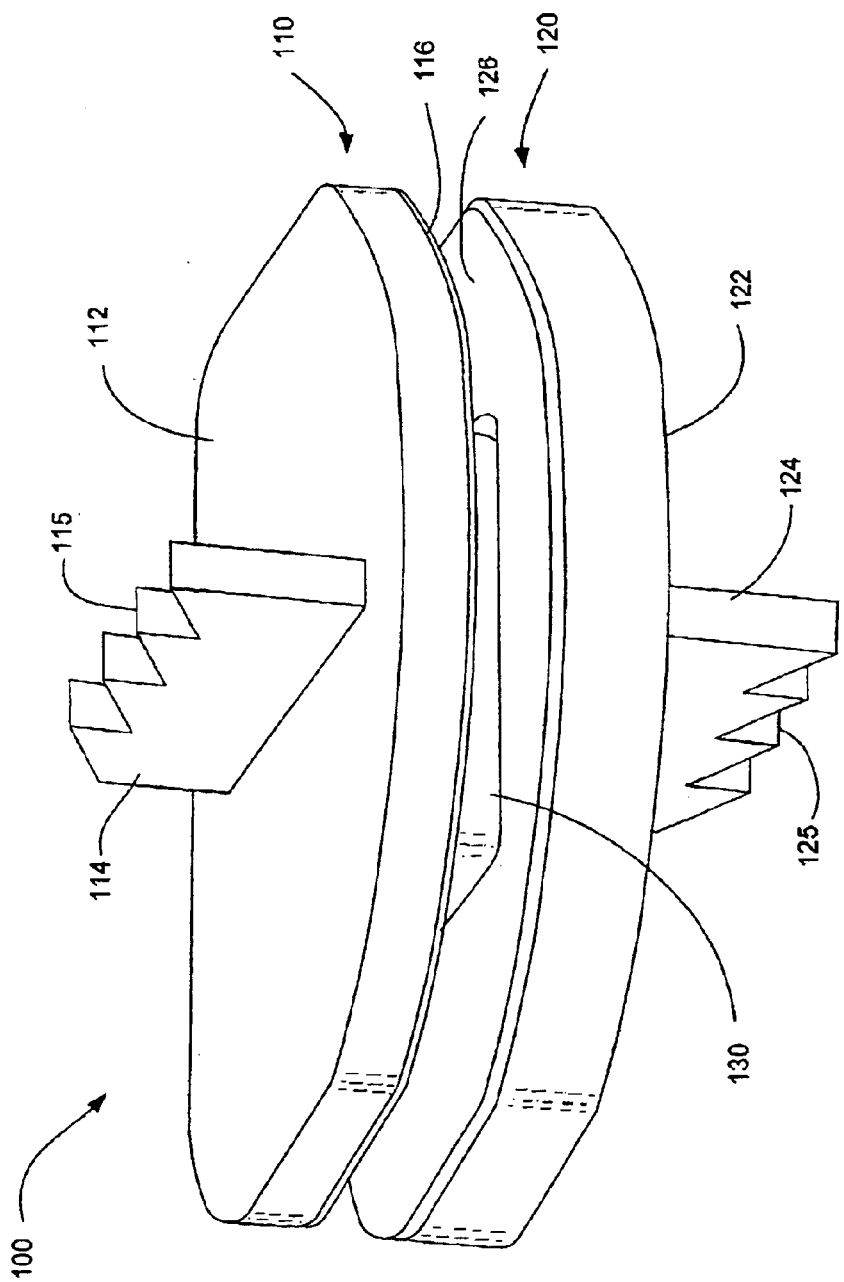
FIG. 1B is an alternative side perspective view of an embodiment of the assembled implant of the invention.

FIG. 1B shows an alternative perspective view of the implant 100 of the invention shown in FIG. 1A. Again, the implant 100 has a first part 110 that is configured to mate with a first vertebra and a second part 120 that is configured to mate with a second vertebra. The third part 130 acts as a spacer to separate the first part 110 from the second part 120 and to allow the first plate 110 and the second plate 120 to pivot or rotate relative to each other.

Figure 2A:
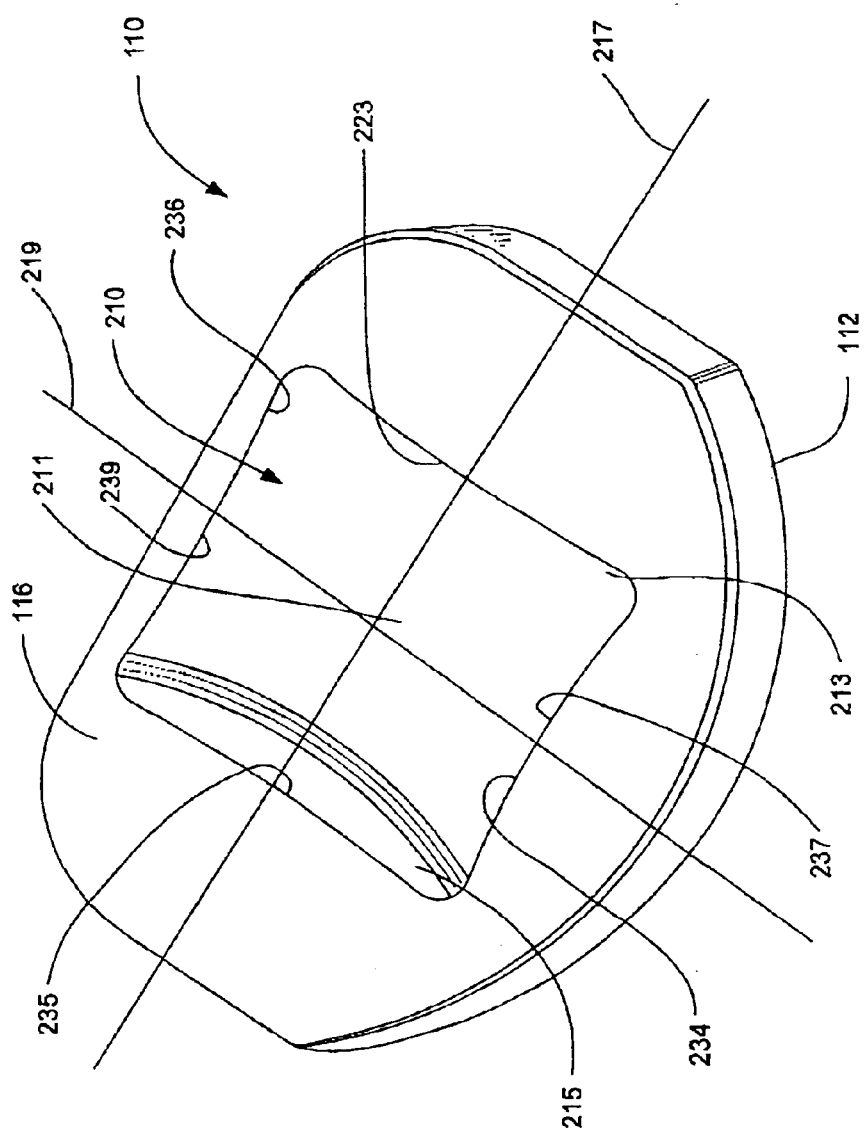
FIG. 2A and FIG. 2B show perspective views of the facing surfaces of the first plate and the second plate of an embodiment of the implant of the invention.

FIG. 2A shows a perspective view of the top plate 110 of the implant 100 of the invention. The first surface 112 of the top plate 110 is configured to contact the vertebral body when the implant 100 is implanted. The first surface 112 has a first keel 114 extending therefrom (shown in FIGS. 1A and 1B). The second surface 116 of the top plate 110 has a cavity 210 or socket formed thereon. The cavity is a convex cylindrical surface. An example of the relative dimensions of the cavity 210, are discussed with respect to FIG. 2C and FIG. 2D below. The cavity 210 includes the shallow convex surface 211 with ends 213 and 215 that are, in this particular embodiment, substantially perpendicular to the surface 116. These ends 213 and 215 essentially form perpendicular ends of a cylindrical void of cavity 210 defined by the convex surface 211 and the ends 213 and 215. As will be described later with respect to the spacer 130, the cavity 210 allows the spacer 130 to pivot or rotate about a first axis 217 that is about perpendicular to the ends 213 and 215 or in other words about an axis for the cylindrical void defined by cavity 210. The ends 213 and 215 block motion of the spacer 130 about a second axis 219 that is perpendicular to the first axis 217. In this embodiment, it is noted that the second axis 219 is parallel to the keels 114 and 124. As can be seen in FIG. 2A, the cavity 210 in this preferred embodiment includes side walls or ends 213 and 215 that have crests 233 and 235 respectively that project into the cavity 210. Additionally, the convex surface 211 has edges 234 and 236 with crests 237 and 239. The crests 233, 235, 237, and 239 allow a loose fit between the spacer 130 and the cavity 210. This loose fit in turn allows the implant to twist in a direction that is perpendicular to the flat plain of the first plate 110 about an axis that is about parallel to the axis of the spine. Thus, the implant 100 allows the spine to have movement in three orthogonal degrees of freedom, namely (1) forward and backward bending movement, (2) lateral side-to-side bending, and (3) twisting movement. It is to be understood that the cavity 240 in the lower plate 120 can also have the same design as the cavity 210 in the upper plate 110 with an increase in the amount of twisting movement afforded by the implant 110. As is noted elsewhere herein, loose fit generally between one or both of the cavities 210 and 240 and the spacer 130 can allow for twisting motion. Further the spacer 130 can also be made with crests on the curved surfaces and on the ends in order to afford similar twisting motion.

Figure 2B:
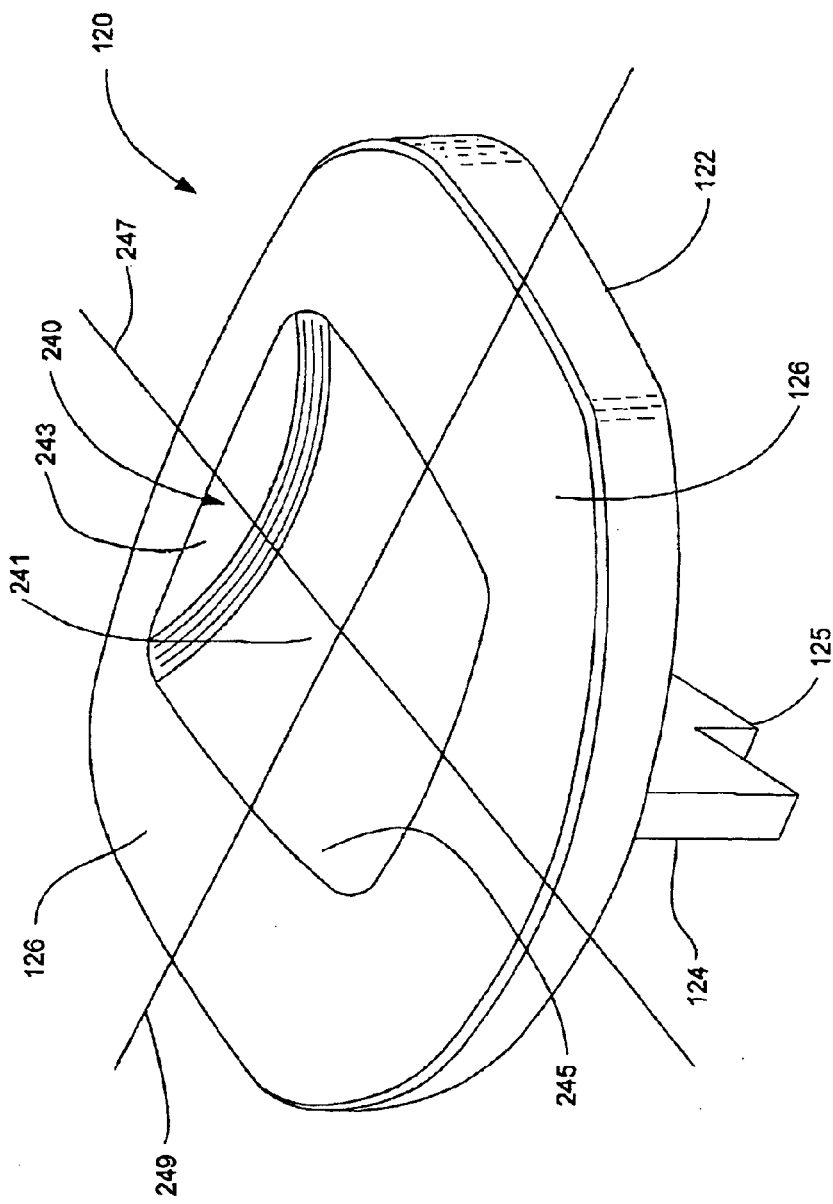

FIG. 2B shows a perspective view of the bottom plate 120 of the implant 100 of the invention. The first surface 122 of the bottom plate 120 is configured to contact the vertebral body when the implant 100 is implanted. As indicated above, the first surface 122 has a second keel 124 extending therefrom. The second surface 126 of the top plate 120 has a cavity 240 or socket formed thereon. The cavity 240 is a convex cylindrical surface. An example of the relative dimensions of the cavity 240 are discussed in more detail with respect to FIG. 2E and FIG. 2F below. The cavity 240 includes the shallow convex surface 241 with ends 243 and 245 that are in this particular embodiment substantially perpendicular to the surface 126. These ends 243 and 245 essentially form perpendicular ends of a cylindrical void of cavity 241 defined by the convex surface 241 and the ends 243 and 245. As will be described later with respect to the spacer 130, the cavity 240 allows the spacer 130 to pivot or rotate about a first axis 247 that is about perpendicular to the ends 243 and 245 or, in other words, about an axis for the cylindrical void defined by cavity 240. The ends 243 and 245 block motion of the spacer 130 about a second axis 249 that is perpendicular to the first axis 247. In this embodiment, it is noted that the first axis 247 is parallel to the keels 114 and 124. It is also noted that in this embodiment the first axis 247 for second plate 120 about which the spacer 130 can pivot or rotate is perpendicular to the first axis 217 of the first plate 110 about which the spacer 130 can pivot or rotate. Thus, as will also be described below, the cavity of the first or upper plate 110 blocks movement of the spacer in a direction that is perpendicular to the keels 114 and 124 while allowing the first plate 110 to pivot or rotate about the first axis 217, an axis that is perpendicular to the keels 114 and 124. In this particular embodiment, generally, the spacer 130 is not required to move in order to emulate the degrees of freedom associated with the back as the ends of the cavities 210 and 240 block movement of the spacer 130. However, it is to be understood that in a preferred embodiment, the fit of the spacer in the cavities 210 and 240 can be loose allowing the spacer to allow the first plate 210 to be able to twist somewhat relative to the second plate 240. This twisting action would generally be about an axis that is perpendicular to the facing surfaces 116 and 126 of the first and second plates 110 and 120, respectively. In other embodiments, the fit can be tighter in order to restrict such twisting action.

Figure 2C:
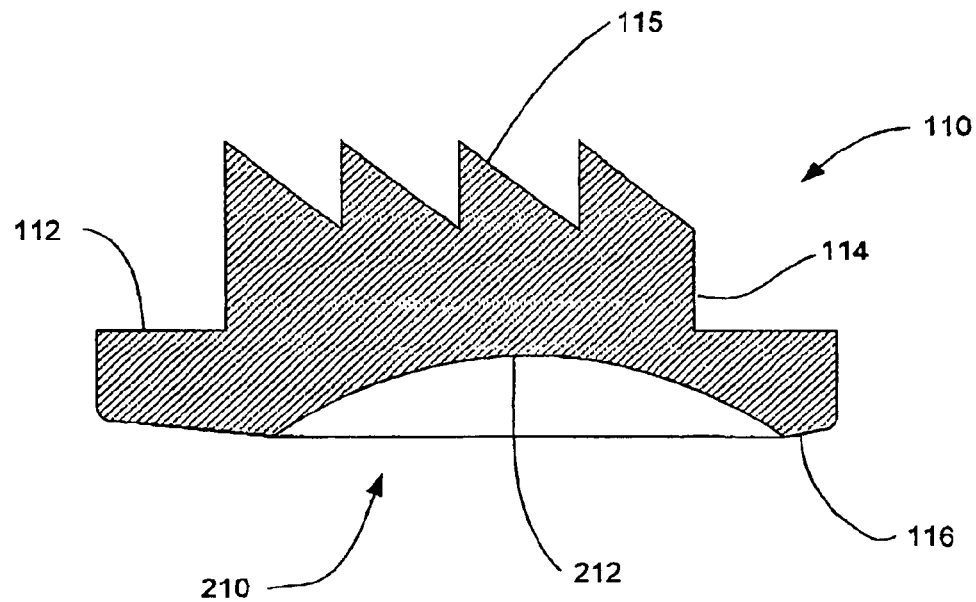
FIG. 2C through FIG. 2F show cross-sectional views of the first plate and the second plate of an embodiment of the implant of the invention.
Figure 2D:
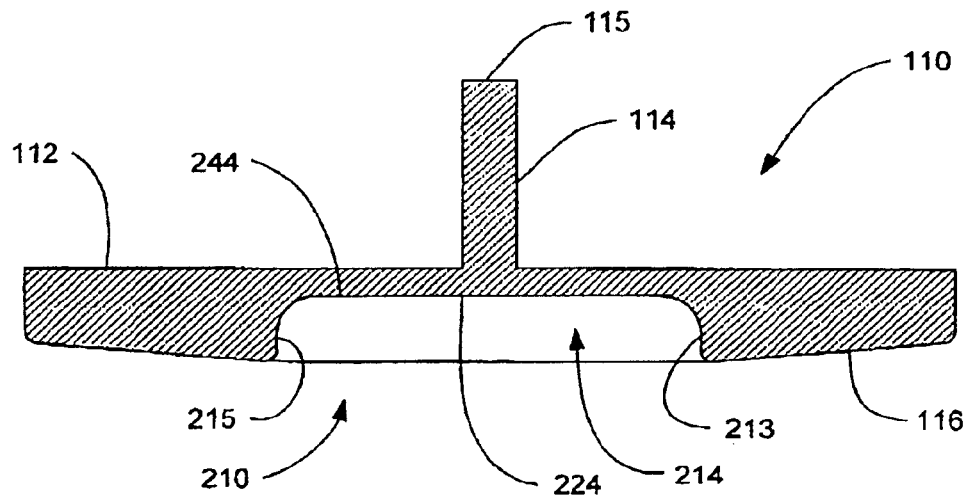

Turning now to FIG. 2C and FIG. 2D, a cross-section of the top plate 110 of the implant 100 of the invention is shown. FIG. 2C is a cross-section taken along a plane that would correspond to a plane that is parallel to the median sagittal plane of the body after the implant was implanted. The first surface 112 of the plate is configured to contact the vertebral body when the implant 100 is implanted. The first surface 112 has a first keel 114 extending therefrom that extends into the vertebral body when implanted. The second surface 116 of the upper plate 110 has a cavity 210 formed thereon. In this figure, the cavity 210 has a first dimension 212. In the first dimension 212, the cavity 210 is concave such that it is curved like the inner surface of a cylinder.

FIG. 2D is a cross-section taken along a plane that would correspond to a plane that is parallel to the frontal (coronal) plane of the body after the implant was implanted. FIG. 2D also illustrates the first surface 112 of the plate with the first keel 114. The second surface 116 of the upper plate 110 has a cavity 210 formed thereon. The cavity 210 has a second dimension 214. The second dimension 214 is in the form of a trough or "flattened-U" with a previously indicated concave bottom surface 211 and two ends or sidewalls 213, 215. As shown in FIG. 2C, the ends or sidewalls 213, 215 are parallel to each other and perpendicular to the bottom surface 211. However, as will be appreciated by those of skill in the art, the ends or sidewalls 213, 215 can be formed at an angle relative to each other without departing from the scope of the invention.

FIG. 2C and FIG. 2D are oriented to illustrate that the first dimension 212 shown in FIG. 2C and the second dimension 214 shown in FIG. 2D are perpendicular to each other.

Figure 2E:
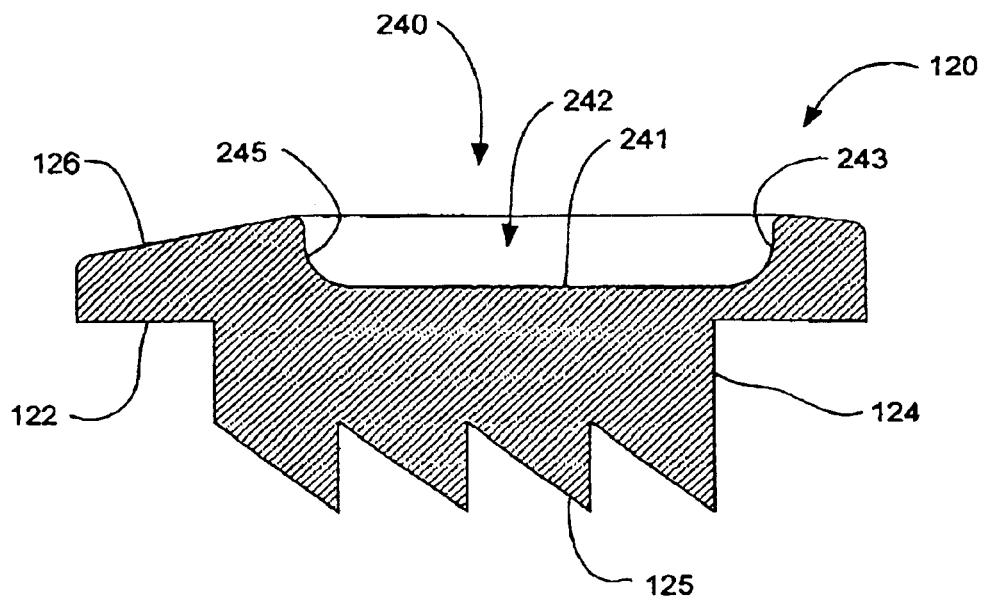
Figure 2F:
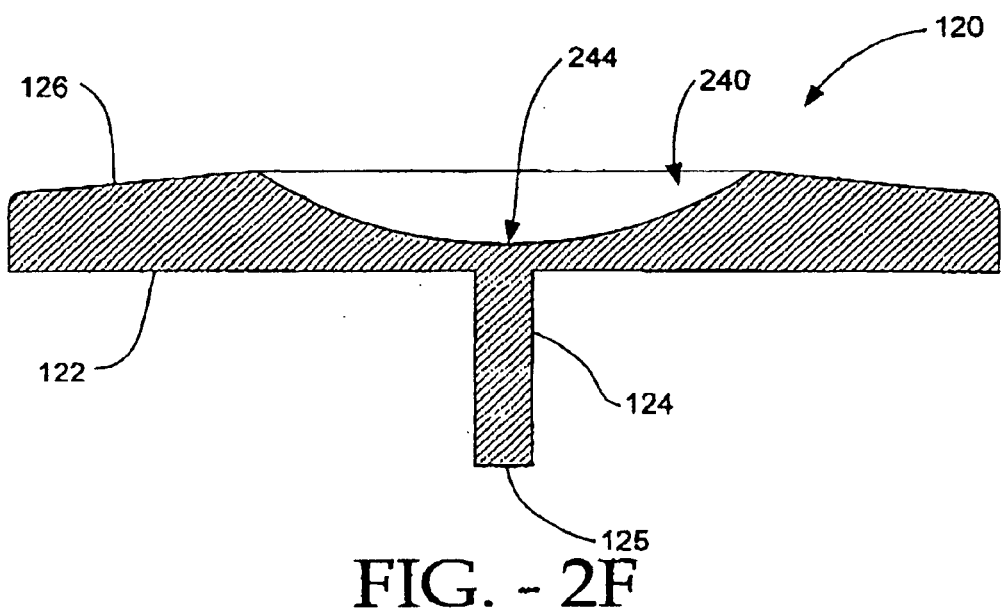

Turning now to FIG. 2E and FIG. 2F, a cross-section of the lower plate 120 of an embodiment of the implant 100 of the invention is shown. FIG. 2E is a cross-section taken along a plane that would correspond to a plane that is parallel to the median sagittal plane of the body after the implant was implanted. FIG. 2E also illustrates the first surface 122 of the bottom plate 122 with the second keel 124. The cavity 240 has a first dimension 242. The first dimension 242 is in the form of a trough or "flattened-U" with a bottom concave surface 241 and two ends or sidewalls 243, 245. As shown in FIG. 2E, the ends or sidewalls 243, 245 are parallel to each other and perpendicular to the bottom surface 241. However, as will be appreciated by those of skill in the art, the ends or sidewalls 243, 245 can be formed at an angle relative to each other without departing from the scope of the invention.

FIG. 2F is a cross-section taken along a plane that would correspond to a plane that is parallel to the frontal (coronal) plane of the body after the implant was implanted. The first surface 122 of the plate is configured to contact the vertebral body when the implant 100 is implanted. The first surface 122 has a first keel 124 extending therefrom. The second surface 126 of the bottom plate 120 has a cavity 240 formed thereon. In this figure, the cavity 240 has a second dimension 244. In the second dimension 244, the cavity 240 is concave such that it is curved like the inner surface of a cylinder.

FIG. 2C and FIG. 2D are oriented to illustrate that the first dimension 212 shown in FIG. 2C and the second dimension 214 shown in FIG. 2D are perpendicular to each other, while FIG. 2E and FIG. 2F illustrate that the first dimension 242 is perpendicular to second dimension 244. Further, the curved first dimension 212 of FIG. 2C is oriented perpendicularly to the curved second dimension 244 of FIG. 2F, while the trough dimension 214 of FIG. 2D is oriented perpendicularly to the trough dimension 242 of FIG. 2E. It is noted that in FIGS. 2C through 2F that the facing surfaces 116 and 126 of the first and second plates are not parallel as shown in the other figures. In these figures the surfaces slope away from the first and second cavities 210 and 240, respectively, in order to provide for a larger range of motion between the first and second plates.

Figure 3A:
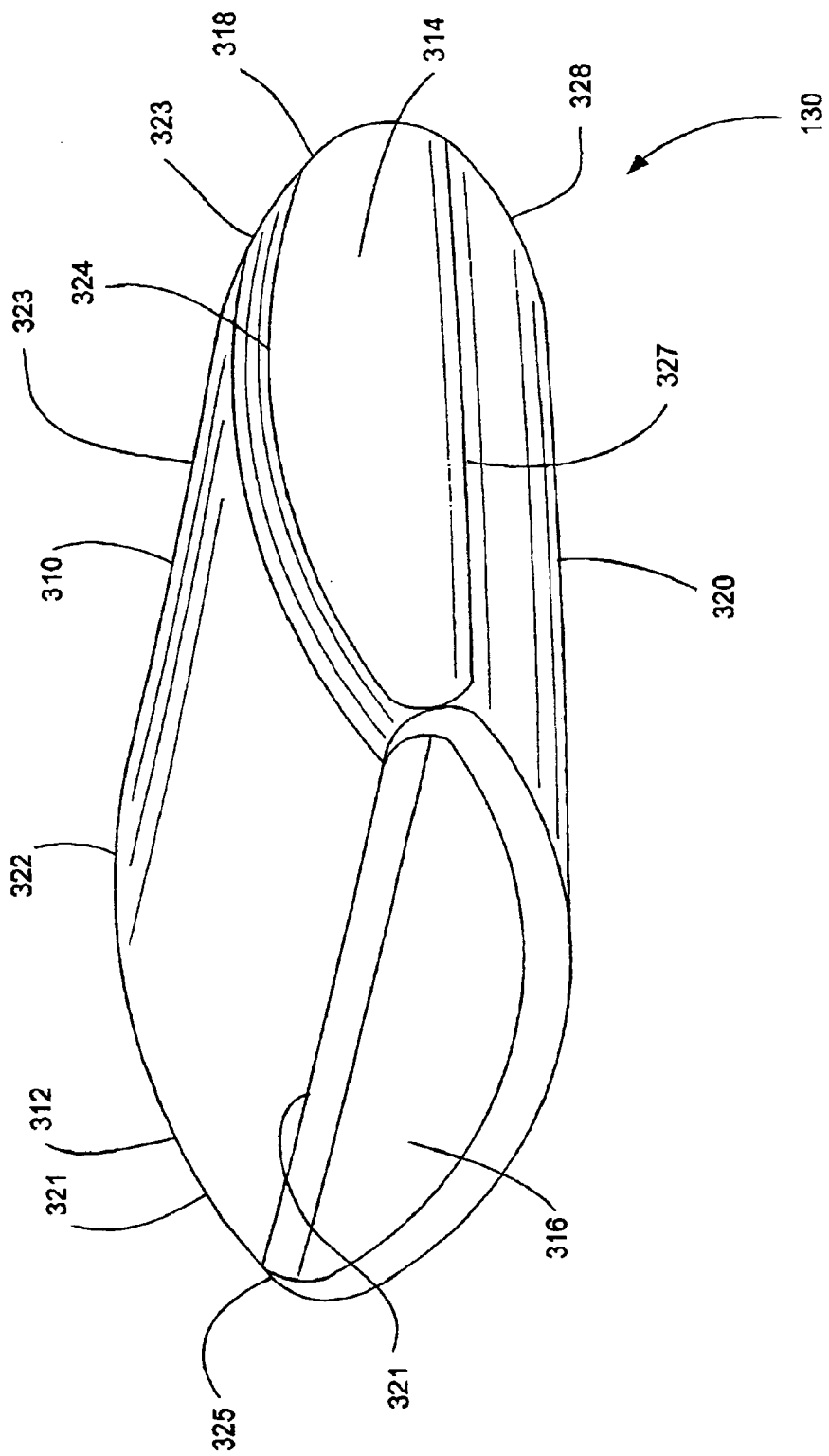
FIG. 3A is a perspective view of the spacer of an embodiment of the implant of the invention.

In FIG. 3A, the spacer 130 is depicted in perspective view. The spacer 130 is dimensioned so that it has a curved or convex upper surface 310 and a curved or convex lower surface 320, respectively, corresponding with the opposing concave surfaces in the upper plate 110 and the lower plate 120.

As shown in FIG. 3A, the curved upper surface 310 is bordered along its curved edge by a pair of first sides 312, 314 that are parallel to each other and along its flat edge by a pair of second sides 316, 318 that are parallel to each other and perpendicular to the pair of first sides 312, 314. The orientation of the pair of first sides 312, 314 to the pair of second sides 316, 318 is such that the curved upper edges 322, 324 of the first sides 312, 314 extend toward the ends of the flat edges 321, 323 of the pair of second sides 316, 318. The curved lower edges 326, 328 extend to meet the ends of the flat edges 325, 327 of the first sides 312, 314.

Figure 3B:
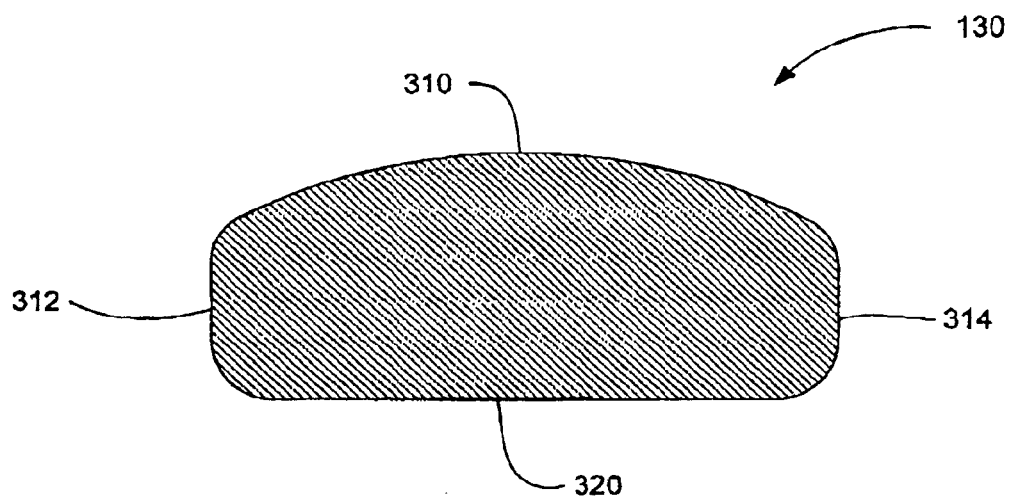
FIG. 3B and FIG. 3C are cross-sections of the spacer of an embodiment of the implant of the invention taken at 90° angles respective to each other.
Figure 3C:
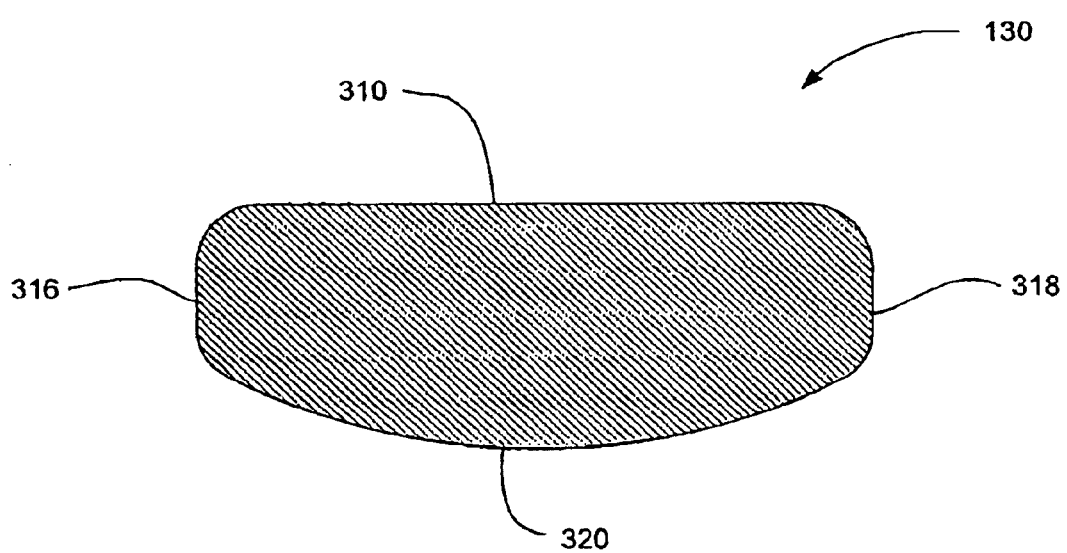

FIG. 3B and FIG. 3C show cross-sections of the spacer 130, shown in FIG. 3A. The cross-section of FIG. 3B is taken at a 90° angle from the cross-section shown in FIG. 3C. FIG. 3B is taken through a plane parallel to the ends 312, 314 and FIG. 3C is taken through a plane parallel to ends 316, 318. The spacer 130 has a concave upper surface 310 and a concave lower surface 320 and pairs of parallel sides 312, 314 and 314, 318.

Figure 4A:
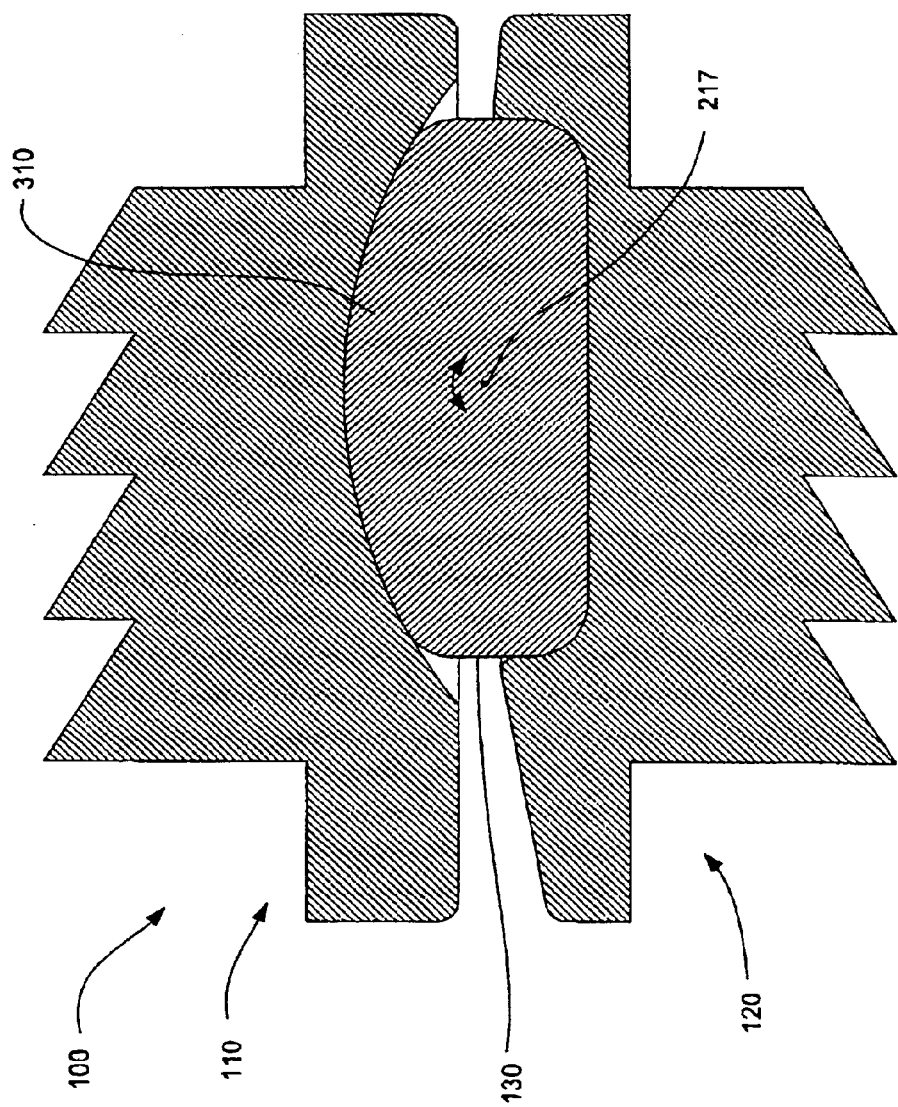
FIG. 4A is a cross-section of an embodiment of the implant of the invention taken along a plane parallel to the sagittal plane.

FIG. 4A shows a cross-section of the implant 100 in its assembled condition taken along a plane that would correspond to a plane that is parallel to the median sagittal plane of the body after the implant was implanted. The implant 100 has a first upper plate 110 that is configured to mate with a first vertebra and a second lower plate 120 that is configured to mate with a second vertebra. The spacer 130 sits between the first plate 110 and the second plate 120.

Figure 4B:
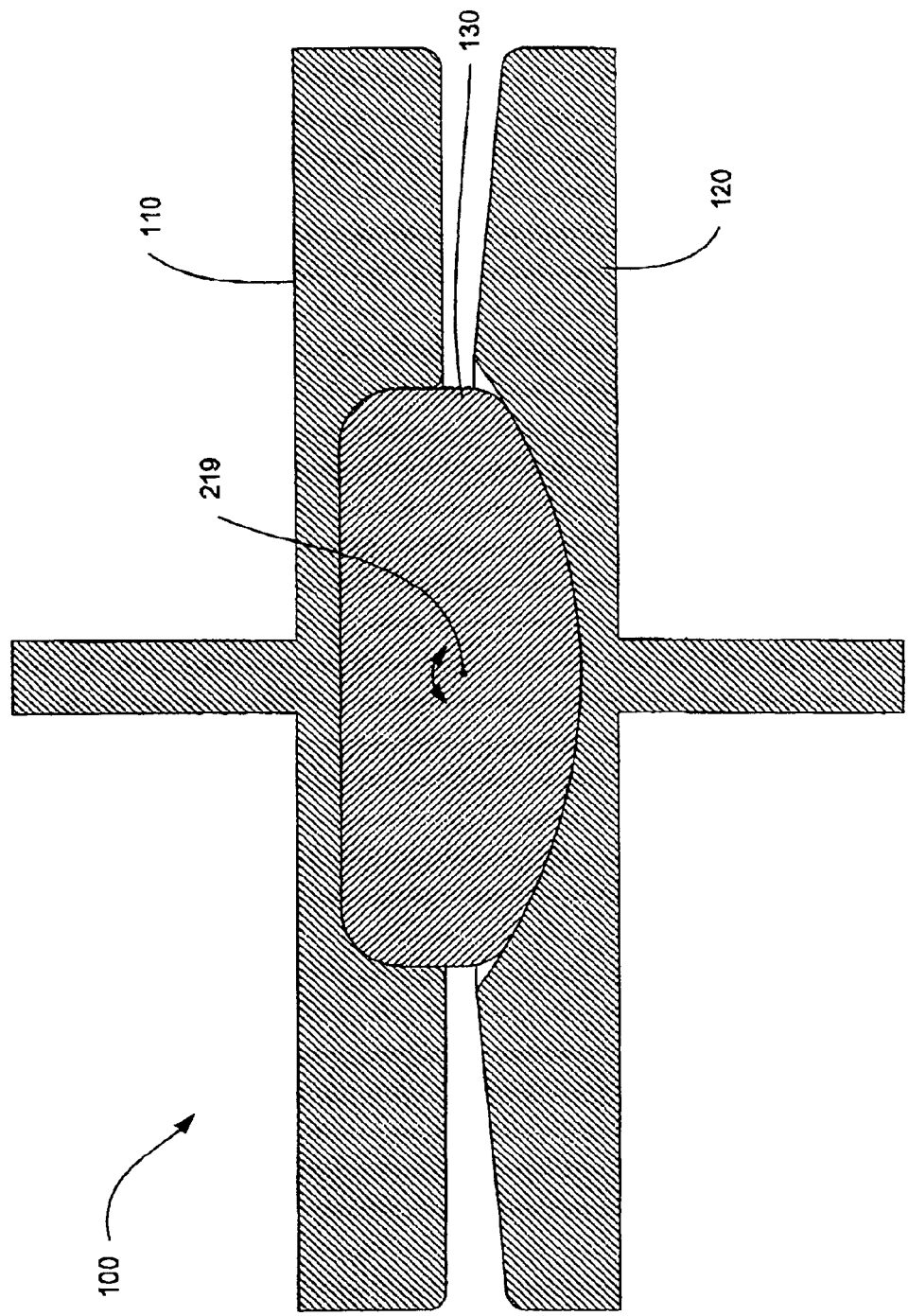
FIG. 4B is a cross-section of an embodiment of the implant of the invention corresponding to a plane parallel to the location of the coronal plane after the implant has been implanted.

FIG. 4B shows a cross-section of the implant 100 in its assembled condition taken at 90° from the cross-section shown in FIG. 4A. Thus, the view of FIG. 4B is taken along a plane that would correspond to a plane that is parallel to the frontal (coronal) plane of the body after the implant was implanted.

It is to be understood that the embodiments of the invention can be made of titanium or medical guide stainless steel or other material that is approved for implantation in a patient and has appropriate characteristics. Alternatively, the spacer 130 can be made out of a polymer, and more specifically, the polymer is a thermoplastic with the other components made of the materials specified above. Still more specifically, the polymer is a polyketone known as polyetheretherketone (PEEK). Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). The spacer 130 can be formed by extrusion, injection, compression molding and/or machining techniques. This material has appropriate physical and mechanical properties and is suitable for carrying and spreading the physical load between the spinous process. Further in this embodiment, the PEEK has the following additional approximate properties:

| PROPERTY | VALUE |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

The spacer can also be comprised of polyetherketoneketone (PEKK). Other material that can be used include polyetherketone (PEK), polyetherketoneetherketoneketone (PEKEKK), and polyetherketoneketone (PEEKK), and, generally, a polyaryletheretherketone. Further, other polyketones can be used as well as other thermoplastics.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

In operation, the implant 100 enables a forward bending movement and a rearward bending movement by sliding the upper plate 110 forward and backward over the spacer 130 relative to the lower plate 120. This movement is shown as rotation about the axis 217 in FIG. 4A.

The implant 100 enables a right lateral bending movement and a left lateral bending movement by sliding the lower plate 120 side-to-side over the spacer 130 relative to upper plate 110. This movement is shown as rotation about the axis 219 in FIG. 4B. Additionally, with a loose fit between the first plate, the second plate and the spacer, rotational or twisting motion along an axis that is along the spine and perpendicular to the first and second plates is accomplished.

To implant the implant 100 of this invention, the spine is exposed and then the intervertebral disk is removed. The implant is then inserted between two vertebrae and the wound is closed. This procedure can be followed for either an anterior approach or posterior approach. For an anterior approach, which due to the anatomy of the body may be preferred, the teeth would be pointed toward the anterior in order to aid in retaining the implant in place. For a posterior approach, the teeth would point posteriorly.

Additional steps, such as cutting channels into the vertebral bodies to accept the keels of the plates and assembling the implant by inserting the spacer between the upper and lower plate prior to installation can also be performed without departing from the scope of the invention.

It is to be appreciated that although the first and second plates are depicted as having concave cavities and the spacer is depicted as having two convex surfaces that are oriented about perpendicular to each other, that other embodiments of the invention can have other configurations. For example, the first and second plates can have convex protrusions, such as, for example, cylindrical protrusions that are shaped to mate with concave surfaces of a spacer, with the concave surfaces of the spacer oriented about perpendicular to each other. In this embodiment, the convex protrusions of the first and the second plates could preferably each have a pair of parallel side walls that would act as the side walls in the depicted embodiments in order to block motion of the spacer. Also, it is to be appreciated that in still another embodiment, the spacer can have upper and lower truncated convex spherical surfaces with two pairs of side walls, instead of cylindrical surfaces with side walls, and be in the scope and spirit of the invention. In this embodiment, each of the first and second plates would have truncated concave spherical surfaces with a pair of side walls. In still a further embodiment, each of the first and second plates could have spherical protrusions with a pair of side walls and the spacer could have first and second spherical concave surfaces with two pairs of side walls joining the first and second spherical concave surfaces. Still alternatively, the first plate can have a concave surface and blocking side walls and the mating portion of the spacer can be convex with the second plate having a convex protrusion with the mating portion of the spacer, or being concave, with blocking side walls.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

What is claimed:

1. An intervertebral implant comprising:
   a first part that is adapted to mate with a first vertebra;
   a second part that is adapted to mate with a second vertebra; and
   a non-symmetrical third part that mates with the first part and the second part, with the third part having a first curved surface that mates with the first part and oriented about a first axis, and a second curved surface that mates with the second part and oriented about a second axis and with the first axis of the first curved surface provided substantially perpendicular to the second axis of the second curved surface.

2. The implant of claim 1 wherein the first part has a first socket that receives the first curved surface and the second part has a second socket that receives the second curved surface.

3. The implant of claim 2 wherein at least one of the sockets has one or more crests.

4. The implant of claim 2 wherein at least one of the sockets has one or more crests to allow for twisting motion between the first part and the second part.

5. The implant of claim 1 wherein the first part has a first keel that is adapted to be inserted in a first vertebra and the second part has a second keel that is adapted to be inserted in a second vertebra.

6. The implant of claim 5 wherein the first and second keels are about parallel to a first axis of movement of one of the first part and the second part about the third part and the first and second keels are about perpendicular to a second axis of movement of the other of the first part and the second part about the third part.

7. The implant of claim 6 wherein the first part has a first socket that receives the first curved surface and the second part has a second socket that receives the second curved surface.

8. The implant of claim 1 wherein the first curved surface allows the implant to move between anterior and posterior directions and the second curved surface allows the implant to move laterally.

9. The implant of claim 1 wherein a material of the third part is selected from the group consisting of polyetheretherketone, polyetherketoneketone, polyaryletheretherketone, polyetherketone, polyetherketoneetherketone-ketone, and polyetheretherketoneketone.

10. An intervertebral implant comprising:
    a first part that is adapted to mate with a first vertebra;
    a second part that is adapted to mate with a second vertebra; and
    a non-symmetrical third part that mates with the first part and the second part with the third part further comprising:
       a first convex surface that mates with the first part configured to limit movement of the first part between a first and second direction about a first axis; and
       a second convex surface that mates with the second part configured to limit movement of the second part between a third and fourth direction about a second axis, wherein the first and second axes are substantially perpendicular to one another.

11. The implant of claim 10 wherein:
    the first part has a first socket that receives the first convex surface and the second part has a second socket that receives the second convex surface.

12. The implant of claim 11 wherein at least one of the sockets has one or more crests.

13. The implant of claim 11 wherein at least one of the sockets has one or more crests to allow for twisting motion between the first part and the second part.

14. The implant of claim 10 wherein the first part has a first keel that is adapted to be inserted in a first vertebra and the second part has a second keel that is adapted to be inserted in a second vertebra.

15. The implant of claim 14 wherein the first and second keels are about parallel to a first axis of movement of one of the first part and the second part about the third part and the first and second keels are about perpendicular to a second axis of movement of the other of the first part and the second part about the third part.

16. The implant of claim 15 wherein:
    the first part has a first socket that receives the first convex surface and the second part has a second socket that receives the second convex surface.

17. The implant of claim 7 wherein the first and second directions are anterior and posterior directions and the third and fourth directions are lateral directions.

18. The implant of claim 10 wherein a material of the third part is selected from the group consisting of polyetheretherketone, polyetherketoneketone, polyaryletheretherketone, polyetherketone, polyetherketoneetherketone-ketone, and polyetheretherketoneketone.

19. An intervertebral implant comprising:
    a first plate adapted to mate to a first vertebral body, the first plate including a first socket having a first interior surface wherein the first interior surface has a curved shape about a first axis;
    a second plate adapted to mate to a second vertebral body, the second plate including a second socket opposed to the first socket, the second socket having a second interior surface, wherein the second interior surface has a curved shape about a second axis oriented substantially perpendicular to the first axis of the curved shape of the first interior surface; and
    a non-symmetrical spacer with a first side that fits adjacent to the curved shape of the first interior surface of the first socket and a second side that fits adjacent to the curved shape of the second interior surface of the second socket.

20. The implant of claim 19 including at least one of the first and second plates including a keel extending therefrom and adapted to engage a vertebral body.

21. The implant of claim 19 including a first keel extending from the first plate and adapted to engage a first vertebral body, and a second keel extending from the second plate and adapted to engage a second vertebral body.

22. The implant of claim 19 wherein the first plate has a first side and a second side, wherein the first side faces the second plate and the second side contacts a surface of the first vertebral body.

23. The implant of claim 22 wherein the first side of the first plate and the second side of the first plate are parallel to each other.

24. The implant of claim 22 wherein the first side of the first plate and the second side of the first plate are not parallel to each other.

25. The implant of claim 19 wherein the second plate has a first side and a second side and the first side of the second plate faces the first plate and the second side of the second plate contacts a surface of the second vertebral body.

26. The implant of claim 25 wherein the first side of the second plate and the second side of the second plate are parallel to each other.

27. The implant of claim 25 the first wherein side of the second plate and the second side of the second plate are not parallel to each other.

28. The implant of claim 19 wherein the first socket of the first plate has first and second side walls that are parallel to each other.

29. The implant of claim 19 wherein the second socket of the second plate has first and second side walls that are parallel to each other.

30. The implant of claim 19 wherein the first and second side walls of the first socket of the first plate are parallel to each other and the second socket of the second plate has first and second side walls that are parallel to each other and further wherein the first and second side walls of the first plate are substantially perpendicular to the first and second side walls of the second plate.

31. The implant of claim 19 wherein the implant is assembled so that the spacer is positioned in the first socket of the first plate and the second socket of the second plate.

32. The implant of claim 19 wherein the first side of the spacer is curved and the second side of the spacer is curved.

33. The implant of claim 32 wherein the first curved side is oriented substantially perpendicular to the second curved side.

34. The implant of claim 19 wherein the first side of the spacer is convex and the second side of the spacer is convex.

35. The implant of claim 34 wherein the convex first side is oriented perpendicular to the convex second side.

36. The implant of claim 19 wherein at least one of the sockets has one or more crests.

37. The implant of claim 19 wherein at least one of the sockets has one or more crests to allow for twisting motion between the first plate and the second plate.

38. The implant of claim 19 wherein a material of the spacer is selected from the group consisting of polyetheretherketone, polyetherketoneketone, polyaryletheretherketone, polyetherketone, polyetherketoneetherketone-ketone, and polyetheretherketoneketone.

39. An intervertebral implant comprising:
a first plate adapted to mate to a first vertebral body;
a second plate adapted to mate to a second vertebral body; and
a non-symmetrical spacer with a first convex side about a first axis and a second convex side about a second axis wherein the first axis of the first convex side is substantially perpendicular to the second axis of the second convex side, wherein first convex side limits movement of the first plate to flexion and extension and the second convex side limits movement of the second plate to lateral bending.

40. The implant of claim 39 including at least one of the first and second plates including a keel extending therefrom and adapted to engage a vertebral body.

41. The implant of claim 39 including a first keel extending from the first plate and adapted to engage the first vertebral body, and a second keel extending from the second plate and adapted to engage the second vertebral body.

42. The implant of claim 39 wherein the first plate has a first side and a second side, wherein the first side faces the second plate and the second side contacts a surface of the first vertebral body.

43. The implant of claim 42 wherein a first socket of the first plate has first and second side walls that are substantially perpendicular to the first side of the first plate.

44. The implant of claim 43 wherein the first socket of the first plate has a curved third side between the first and second side walls.

45. The implant of claim 39 wherein a socket of the first plate has first and second side walls that are parallel to each other.

46. The implant of claim 39 wherein the second plate has a first side and a second side, wherein the first side faces the first plate and the second side contacts a surface of the second vertebral body.

47. The implant of claim 46 wherein the first side of the second plate and the second side of the second plate are parallel to each other.

48. The implant of claim 46 wherein the first side of the second plate and the second side of the second plate are not parallel to each other.

49. The implant of claim 46 wherein a socket of the second plate has first and second side walls that are substantially perpendicular to the first side of the second plate.

50. The implant of claim 39 wherein a second socket of the second plate has first and second side walls that are parallel to each other.

51. The implant of claim 39 wherein the first plate is adapted to mate to an upper vertebral body.

52. The implant of claim 51 wherein the second plate is adapted to mate to a lower vertebral body.

53. The implant of claim 39 wherein the first plate is adapted to mate to a lower vertebral body.

54. The implant of claim 53 wherein the second plate is adapted to mate to an upper vertebral body.

55. An intervertebral implant comprising:
a first plate adapted to mate with a first vertebra;
a second plate adapted to mate with a second vertebra;
a spacer between the first and the second plates along a transverse plane;
the spacer non-symmetrical about the transverse plane and having first and second curved surfaces that are at an angle to each other with the first curved surface mated with the first plate and the second curved surface mated with the second plate.

56. The implant of claim 55 wherein the curved surfaces are cylindrical.

57. The implant of claim 56 wherein the first and second plates each have a cylindrical surface that mates with a respective cylindrical surface of the spacer.

58. The implant of claim 55 wherein the curved surfaces are convex.

59. The implant of claims 58 wherein the first and second plates each have a concave surface that mates with a respective convex surface of the spacer.

60. The implant of claim 55 wherein the first and second plates each have a curved surface that mates with a respective curved surface of the spacer.

61. The implant of claim 55 wherein the first curved surface has a first axis and the second curved surface has a second axis, and the first axis and the second axis are at an angle to each other.

62. The implant of claim 55 wherein the first curved surface has a first axis and the second curved surface has a second axis, and the first axis and the second axis are at about perpendicular to each other.

63. An intervertebral implant comprising:
a first plate adapted to mate with a first vertebra;
a second plate adapted to mate with a second vertebra;
a spacer placed between the first and the second plates; and
wherein said spacer in conjunction with the first plate allows rotational motion about a first axis and blocks motion about a second axis, and the spacer in conjunction with the second plate allows rotational motion about the second axis and blocks motion about the first axis.

64. The implant of claim 63 wherein said first axis is perpendicular to the second axis.

65. The implant of claim 63 wherein the implant can rotate about a third axis that is at an angle to the first axis and to the second axis.

66. An intervertebral implant comprising:
a first plate including a first curved interior surface extending between a first end and a second end of the first plate;
a second plate including a second curved interior surface extending between a third end and a fourth end of the second plate, wherein the third and fourth ends are oriented substantially perpendicular to the first and second ends; and
a spacer positioned between the first plate and the second plate substantially along a transverse plane, the spacer having a non-symmetrical configuration about the transverse plane, wherein the spacer includes a first convex surface in contact with the first curved interior surface and a second convex surface in contact with the second curved interior surface.

67. The implant of claim 66 including at least one of the first and second plates including a keel extending therefrom and adapted to engage a vertebral body.

68. The implant of claim 66 including a first keel extending from the first plate and adapted to engage the first vertebral body, and a second keel extending from the second plate and adapted to engage the second vertebral body.

69. The implant of claim 66 wherein the first plate has a first side and a second side, wherein the first side faces the second plate and the second side contacts a surface of the first vertebral body.

70. The implant of claim 69 wherein the first side of the first plate and the second side of the first plate are parallel to each other.

71. The implant of claim 69 wherein the first side of the first plate and the second side of the first plate are not parallel to each other.

72. The implant of claim 69 wherein the first curved interior surface of the first plate has first and second side walls that are substantially perpendicular to the second side of the first plate.

73. The implant of claim 66 wherein the first curved interior surface of the first plate has a first side wall and a second side wall, wherein the first and second side walls limit movement of the first plate in a desired direction with respect to the spacer.

74. The implant of claim 73 wherein the first and second side walls of the first plate are parallel to each other.

75. The implant of claim 74 wherein the second curved interior surface of the second plate has first and second side walls that are substantially perpendicular to the first and second side walls of the first plate.

76. The implant of claim 66 wherein the first curved interior surface of the first plate has first and second side walls that are parallel to each other and the first and second side walls of the second curved interior surface are parallel to each other and further wherein the first and second side walls of the first plate are substantially perpendicular to the first and second side walls of the second plate.

77. The implant of claim 66 wherein the second plate has a first side and a second side and the first side of the second plate faces the first plate and the second side of the second plate contacts a surface of the second vertebral body.

78. The implant of claim 77 wherein the first side of the second plate and the second side of the second plate are parallel to each other.

79. The implant of claim 77 wherein the first side of the second plate and the second side of the second plate are not parallel to each other.

80. The implant of claim 66 wherein the first convex surface of the spacer is substantially perpendicular to the second convex surface of the spacer.

81. The implant of claim 66 wherein the first convex surface is oriented to lie substantially perpendicular to the second convex surface.

82. The implant of claim 66 wherein a material of the spacer is selected from the group consisting of polyetheretherketone, polyetherketoneketone, polyaryletheretherketone, polyetherketone, polyetherketoneetherketone-ketone, and polyetheretherketoneketone.

83. An intervertebral implant comprising:
a first plate adapted to mate with a first vertebra, the first plate further comprising:
a first socket therein having a first concave surface;
a first wall adjacent to the first concave surface;
a second wall adjacent to the first concave surface;
a second plate adapted to mate with a second vertebra, the second plate further comprising:
a second socket therein having a second concave surface, the second socket opposed to the first socket, wherein the second concave surface is oriented substantially perpendicular to the first concave surface;
a third wall adjacent to the second concave surface;
a fourth wall adjacent to second concave surface, wherein the third and fourth walls are substantially perpendicular to the first and second walls;
a non-symmetrical spacer having a first convex surface to be received in the first socket and a second convex surface to be received in the second socket, wherein the first socket limits movement of the first plate between a first and second direction and the second socket limits movement of the second plate between a third and fourth direction.

84. An intervertebral implant having an anterior side, a posterior side, a right lateral side and a left lateral side, the implant comprising: a non-symmetrical spacer between a first plate and a second plate, the spacer having a first convex surface oriented between the anterior side and the posterior side and mated with the first plate, the spacer having a second convex surface opposed to the first convex surface and mated with the second plate, wherein the second convex surface is oriented between the right lateral side and the left lateral side.

85. An intervertebral implant having an anterior side, a posterior side, a right lateral side and a left lateral side, the implant comprising: a spacer between a first plate and a second plate, the spacer having a first convex surface oriented such that the first plate is limited to rotating about a first axis intersecting the right and left lateral sides, the spacer further having a second convex surface opposed to the first convex surface oriented such that the second plate is limited to rotating about a second axis intersecting the anterior and posterior sides.

86. An intervertebral implant comprising:
   a first part that is adapted to mate with a first vertebral body;
   a second part that is adapted to mate with a second vertebral body; and
   a third part that mates with the first part and the second part, with the third part having a first curved surface adapted to mate with the first part and provided about a first axis, the first curved surface to allow the implant to move substantially between anterior and posterior directions and a second curved surface adapted to mate with the second part and provided about a second axis, the second curved surface to allow the implant to move substantially laterally, wherein the first axis and the second axis are oriented at an angle with respect to one another.

87. The implant of claim 86 wherein the first part and the second part are rotatable about a third axis substantially perpendicular to the first and second axes.

88. The implant of claim 86 wherein the first axis is substantially perpendicular to the second axis.

89. An intervertebral implant comprising:
   a first part that is adapted to mate with a first vertebra;
   a second part that is adapted to mate with a second vertebra; and
   an non-symmetrical third part that mates with the first part and the second part with the third part further comprising:
      a first surface that mates with the first part configured to limit movement of the first part between a posterior and anterior direction; and
      a second convex surface that mates with the second part configured to limit movement of the second part between lateral directions.

* * * * *

UNITED STATES PATENT AND TRADEMARK OFFICE
CERTIFICATE OF CORRECTION

PATENT NO. : 6,966,929 B2
DATED : November 22, 2005
INVENTOR(S) : James F. Zucherman It is certified that error appears in the above-identified patent and that said Letters Patent is hereby corrected as shown below:

Column 10,
Line 36, change "claim 7" to -- claim 10 --.

Column 11,
Line 20, change "the first wherein side" to -- wherein the first side --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,966,929 B2  
APPLICATION NO. : 10/685011  
DATED : November 22, 2005  
INVENTOR(S) : James F. Zucherman Page 1 of 1

It is certified that error appears in the above-identified patent and that said Letters Patent is hereby corrected as shown below:

At column 10, line 36, change "claim 7" to --claim 10--.

At column 11, line 20, change "the first wherein side" to --wherein the first side--.

Signed and Sealed this

Twenty-sixth Day of February, 2008

JON W. DUDAS  
*Director of the United States Patent and Trademark Office*

UNITED STATES PATENT AND TRADEMARK OFFICE
CERTIFICATE OF CORRECTION

PATENT NO. : 6,966,929 B2  Page 1 of 1
APPLICATION NO. : 10/685011
DATED : November 22, 2005
INVENTOR(S) : Steve Mitchell It is certified that error appears in the above-identified patent and that said Letters Patent is hereby corrected as shown below:

On title page Item [75]
Please change "James F. Zucherman" to --Steve Mitchell--.

Signed and Sealed this

Twelfth Day of August, 2008

JON W. DUDAS
*Director of the United States Patent and Trademark Office*